United States Patent [19]
Fushimi et al.

[11] Patent Number: 5,195,372
[45] Date of Patent: Mar. 23, 1993

[54] ULTRASONIC TESTING METHOD FOR DETECTING FLAWS OF BALLS FOR STRUCTURAL MEMBERS AND APPARATUS FOR SAID METHOD

[75] Inventors: Koji Fushimi, Gifu; Keiji Kawasaki, Nagoya, both of Japan

[73] Assignee: NGK Insulators, Ltd., Nagoya, Japan

[21] Appl. No.: 920,527

[22] Filed: Jul. 28, 1992

Related U.S. Application Data

[63] Continuation of Ser. No. 617,101, Nov. 21, 1990, abandoned.

[30] Foreign Application Priority Data

Nov. 21, 1989 [JP] Japan .................................. 1-302531

[51] Int. Cl.⁵ .............................................. G01N 29/04
[52] U.S. Cl. ............................................ 73/593; 73/640
[58] Field of Search ............... 73/593, 598, 620, 627, 73/640; 340/682

[56] References Cited

U.S. PATENT DOCUMENTS

| | | | |
|---|---|---|---|
| 3,803,904 | 4/1974 | Diem | 73/103 |
| 4,065,960 | 1/1978 | Grabendorfer et al. | 73/627 |
| 4,387,596 | 6/1983 | Fenkner | 73/593 |
| 4,969,361 | 11/1990 | Kawasaki et al. | 73/593 |
| 5,001,674 | 3/1991 | Kawasaki | 73/640 |
| 5,005,417 | 4/1991 | Kawasaki et al. | 73/593 |

FOREIGN PATENT DOCUMENTS

| | | |
|---|---|---|
| 3905430 | 11/1989 | Fed. Rep. of Germany . |
| 2549226 | 1/1985 | France . |
| 60-162952 | 8/1985 | Japan . |
| 2068550 | 8/1981 | United Kingdom . |

Primary Examiner—Louis Arana
Attorney, Agent, or Firm—Shea & Gould

[57] ABSTRACT

An ultrasonic testing method for detecting flaws of balls for structural members comprises rotating a ball to be tested in an ultrasonic wave transmitting medium. At least two focus-type ultrasonic probes are provided and arranged so as to cover nonoverlapping flaw-detecting regions on and/or inside the ball. Flaws in the ball are detected by sending ultrasonic waves from the probes toward the ball. An apparatus for detecting flaws of balls comprises a ball holding portion for rotatably holding the ball to be tested, at least two focus-type probes for detecting flaws and at least two probe mounting portions for mounting the probes thereof so that respective axes of the probes are each capable of being set eccentrically relative to the center of the ball and wherein the focal positions of the probes are variable.

10 Claims, 2 Drawing Sheets

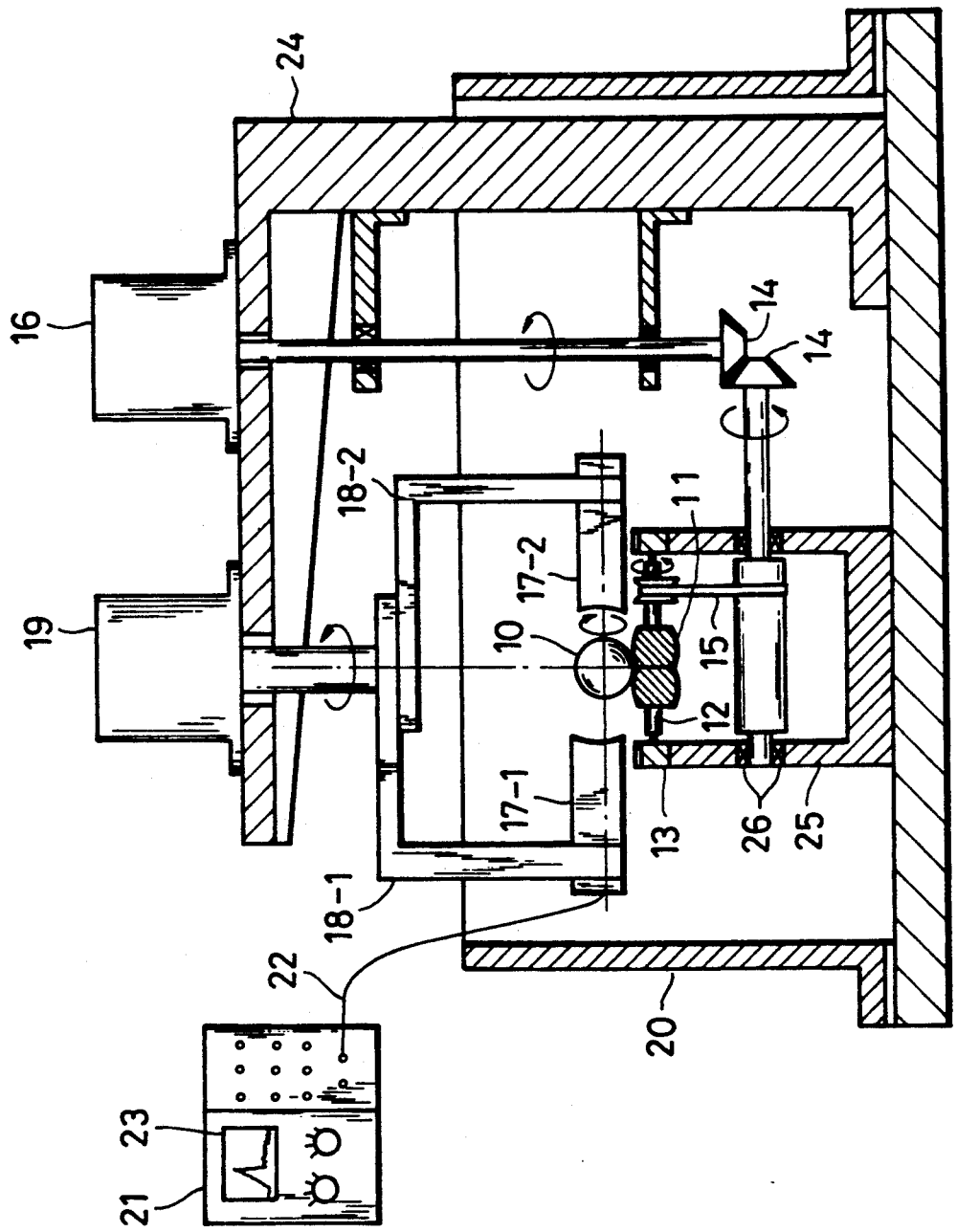

ULTRASONIC TESTING METHOD FOR DETECTING FLAWS OF BALLS FOR STRUCTURAL MEMBERS AND APPARATUS FOR SAID METHOD

This application is a continuation of application Ser. No. 617,101 filed Nov. 21, 1990 now abandoned.

BACKGROUND OF THE INVENTION AND RELATED ART STATEMENT

This invention relates to an ultrasonic testing method and apparatus for detecting flaws of balls for structural members, and more particularly to an ultrasonic testing method for accurate detection of minute flaws in the surface and the inside of balls for structural members, wherein at least two probes are used.

As a testing method for detecting flaws of steel materials, steel plates, forgings, etc., there has been known an immersion-type ultrasonic testing method for detecting flaws in which water is used as a medium for transmitting ultrasonic waves.

In application of the conventional ultrasonic testing method for detecting flaws in products to be or being used under severe conditions, a focus-type probe obtained by attaching a concave resin lens to an oscillator or by forming the oscillator itself in a concave shape has been used to detect flaws several hundreds of micrometers in size, thereby achieving a higher reliability.

On the other hand, research have been conducted on the use of ceramics for bearing members and the like, which are required to have high reliability. Ceramics are brittle materials, and, especially in the case of balls for structural members such as ceramic balls used for bearings which have been being developed in recent years, the presence of flaws such as pores, foreign matter and cracks in a portion of the ball might cause a concentration of stress on that portion, resulting in breakage. The larger the flaws become and the nearer the flaws to the surface of the ball are, the greater the effect of the flaws becomes. Therefore, a testing method with high resolution has been desired for detection of such flaws of the ceramic products.

The present inventors previously proposed, in Japanese Patent Application Laid-Open (KOKAI) No. 63-243751 (1988) (which corresponds to U.S. patent application Ser. No. 172,244) and Japanese Patent Application Laid-Open (KOKAI) No. 1-219554 (1989) (which corresponds to U.S. patent application Ser. No. 07/311,041), an ultrasonic testing method and apparatus for detecting flaws of balls in which a focus-type ultrasonic probe is used with the focus located on the surface of the ball and with the angle of incidence of the ultrasonic waves set equal to the critical angle of the transverse wave, thereby detecting accurately the flaws present in the surface of the ball and the flaws present at a depth of 2 mm from the surface;

Though a higher detection accuracy than that in the prior art is achieved by the ultrasonic testing method for detecting flaws previously proposed by the present inventors, most of the incident ultrasonic waves are reflected by the surface of the ball or are converted into a surface wave and, therefore, only a part of the ultrasonic waves propagate into the inside of the ball. Accordingly, in the previously proposed method, the detection sensitivity for the internal flaws has been lower than that for surface flaws. Because detection of flaws with higher accuracy requires a finer detection pitch, the method has required a long time for performing flaw detection for the entire surface of the ball with higher accuracy.

SUMMARY OF THE INVENTION

It is accordingly an object of this invention to provide an ultrasonic testing method and apparatus therefor for detecting flaws of balls for structural members which enables detection of internal flaws of the balls with higher sensitivity and enables the flaw detection to be performed in a shorter time, without any lowering in detection accuracy.

According to this invention, there is provided an ultrasonic testing method for detecting flaws of balls for structural members which comprises detecting flaws of the ball while the ball is rotated in a medium for transmitting ultrasonic waves, wherein at least two focus-type probes with respective flaw detecting regions which are substantially non-overlapping are disposed with such an eccentricity that the angles of incidence of ultrasonic waves accord with the critical angle of the transverse ultrasonic waves, and the foci of the probes are located on the surface of the ball.

There is also provided, according to this invention, an ultrasonic testing method for detecting flaws of balls for structural members which comprises detecting flaws of the ball while the ball is rotated in a medium for transmitting ultrasonic waves, wherein at least two focus-type probes with respective flaw detecting regions which are substantially non-overlapping are used, at least one of the probes is disposed with such an eccentricity that the angle of incidence of ultrasonic waves accords with the critical angle of the transverse ultrasonic waves, the focus of the at least one of the probes is located on the surface of the ball, whereas the other probe is so disposed that an ultrasonic wave therefrom is perpendicularly incident on the surface of the ball, and the focus of the other probe is located in the inside of the ball.

In this invention, because non-overlapped flaw detecting regions are employed, flaw detecting areas of the probes in the outer surface and/or inside of the ball don't overlap.

According to this invention, there is further provided an ultrasonic testing apparatus for detecting flaws of balls for structural members which comprises a ball holding portion for holding rotatably the ball for structural members, at least two focus-type probes for detection of flaws, and at least two probe mount portions for mounting the probes thereon so that the axes of each of the probes are capable of being set eccentric relative to the center of the ball and the position of the focus of each of the probes is variable.

BRIEF DESCRIPTION OF THE DRAWINGS

FIG. 1 is a sectional view illustrating one embodiment of an ultrasonic testing apparatus for detecting flaws according to this invention;

DETAILED DESCRIPTION OF THE PREFERRED EMBODIMENTS

Figure 2A:
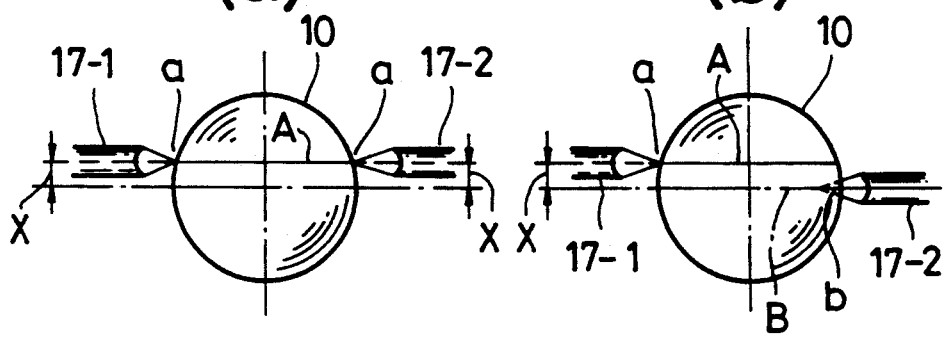
FIGS. 2(a) and 2(b) are each sectional views illustrating the positional relationship between two probes in one embodiment of this invention.

The ultrasonic testing method for detecting flaws according to this invention is carried out in a medium for transmitting ultrasonic waves, and can be carried out effectively by use of an ultrasonic testing apparatus for detecting flaws which comprises a ball holding portion for holding rotatably a ball for structural members, at least two focus-type probes for detection of flaws, and at least two probe mount portions for mounting the probes thereon so that the axes of each of the probes are capable of being set eccentric relative to the center of the ball and the position of the focus of each of the probes is variable.

At least two ultrasonic probes used in this invention for detecting flaws of balls for structural members can be disposed so that each probe for flaw detection is in charge of one section about the periphery of the material to be tested. Namely, the ball for structural members is divided into at least two sections. In this case, at least two probes are each arranged to swivel along the periphery of the ball, and the regions of flaw detection on and/or in the ball are set so as to substantially not overlap with each other. Thus, the probes perform flaw detection separately for the respective sections of the periphery of the ball.

With the above arrangement, it is possible to shorten the flaw detecting time even where a finer detection pitch is adopted.

The number of the probes, which may ordinarily be two, may be appropriately selected according to the testing conditions such as the size of the balls to be tested, the detection pitch, etc.

The probe used in this invention is preferably a focus-type probe in which a tip portion of the probe, namely, an acoustic lens or an oscillator has a spherical surface for providing a focus at which an ultrasonic wave is most intensified. If the probe is not of the focus-type, the ultrasonic wave is scattered in the inside of the ball, resulting in a lower detection sensitivity.

In the ultrasonic testing method for detecting flaws according to this invention, the test for detecting flaws of a ball may be carried out with at least two probes so disposed that the focus of each of the probes is located on the surface of the ball and the center axis of each of the probes is eccentric relative to the center of the ball.

Further, in the ultrasonic testing method for detecting flaws according to this invention, the test for detecting flaws of a ball may be carried out by disposing at least one of the plural probes so as to locate the focus thereof on the surface of the ball, as in the above method, setting the center axis of at least one of the probes eccentric relative to the center of the ball, while setting the center axis of the other probe in conformity with the center of the ball to cause the ultrasonic wave from the other probe to be perpendicularly incident on the surface of the ball, and locating the focus of the other probe in the inside of the ball.

In the ultrasonic testing method for detecting flaws according to this invention, the center axis of each probe may, in some cases, be set eccentric relative to the center axis of the ball or, in other cases, be set to coincide with the center axis of the ball.

Where the center axis of the probe is set eccentrically, the eccentricity may be set at such a value that the angle of incidence of ultrasonic wave becomes equal to the critical angle of the ultrasonic transverse wave. The eccentricity X corresponding to the critical angle of the transverse wave is calculated from the following formula (1):

$$X = R \cdot V_L / V_B \qquad (1)$$

where $V_L$ (m/sec) is the velocity of ultrasonic transverse wave in a liquid, such as water and an oil, used as a medium for transmitting ultrasonic waves in which the ultrasonic testing apparatus for detecting flaws is disposed and $V_B$ (m/sec) is the velocity of ultrasonic longitudinal waves in a ball to be tested having a radius of curvature R (mm).

When the probe is disposed with such an eccentricity, the ultrasonic wave is transmitted along the surface of the ball, so that minute flaws present on the surface of the ball and in the vicinity of the surface can be detected accurately.

When the center axis of the probe is set in conformity with the center of the ball, thereby causing the ultrasonic wave to be perpendicularly incident on the surface of the ball, and the focus of the probe is located in the inside of the ball, it is possible to detect accurately the minute flaws, particularly the minute flaws at the focal position inside the ball.

The two probes of this invention are held respectively by probe mount portions. The probe mount portions are each provided with a mechanism for swiveling along a predetermined horizontal circumference of the spherical surface of the ball. With the probe mount portions operated, the probes mounted on the portions are each swiveled along the peripheral surface of the ball, whereby the ball surface in each flaw detecting region can be tested completely by the probe in charge of the region. In this case, the swiveling range of each probe is set to be an angle of 180° around the ball, whereby the entire peripheral surface of the ball can be tested completely.

Further, the probe mount portion is provided with a mechanism for enabling a movement of a tip portion of the probe through 180° around the ball, setting the position of the probe over the surface of the ball freely in vertical and horizontal directions, and for freely setting the spacing between the probe and the ball. The mechanism makes it possible to conform the center axis of the probe to the center of the ball, or to set the center axis of the probe eccentric relative to the center of the ball, and to locate the focus of the probe on the surface of the ball or in the inside of the ball.

In the testing method for detecting flaws of balls for structural members according to this invention, testing is carried out by rotating the ball in a medium for transmitting ultrasonic waves. For this purpose, the ball holding portion for holding the ball thereon is provided with a mechanism for free rotation of the ball. For instance, four rollers each being circular in vertical cross section are combined to form a recessed portion on which to mount the ball. By rotating the rollers with the ball mounted on the recessed portion, the ball can be rotated. With the ball rotated vertically on a rotational axis parallel to the axis of the probe, the entire peripheral surface of the ball can be tested for flaw detection by swiveling the probe along the peripheral surface of the ball through 180° from one point to another along the rotational axis of the ball. Therefore, where N probes (N is a number of at least two) are disposed with the same eccentricity, the swiveling range of each probe for flaw detection may be as small as 180/N°; accordingly, the flaw detecting time is shortened, and ultrasonic testing for detecting flaws with high accuracy can be achieved by setting a finer detection pitch for each probe.

Furthermore, the recessed portion on which the ball is mounted may be formed by combining rollers of different diameters or combining rollers having differing coefficients of friction, whereby the center of rotation of the ball may be shifted while the ball is rotated in a fixed direction or the ball may be rotated spirally. In such cases, the entire surface of the ball can be tested without swiveling the probes; therefore, two or more probes can be disposed to have foci at different positions relative to the ball surface, for instance, on the ball surface, at a depth of 1 mm from the surface, at a depth of 2 mm, at a depth of 3 mm, and so on, whereby it is possible to detect accurately the flaws on the surface of the ball and in the inside of the ball.

As mentioned above, the probe mount portions and the ball rotating mechanism enable swiveling of the probes along the peripheral surface of the ball, rotation of the ball itself, shifting of the rotational axis of the ball, and spiral rotation of the ball, whereby the entire surface of the ball and the inside of the ball can be completely tested for detecting flaws.

The balls for structural members in this invention may be balls which are used as bearing members, wear-resistant members or sliding members. Though the balls can be made both of a ceramic and of a metal, ceramic balls for structural members are particularly suitable for use as the object to be tested according to this invention because the accurate detection of minute flaws of such ceramic balls has an extremely great effect on the reliability of the balls.

Furthermore, by the ultrasonic testing method and apparatus for detecting flaws of balls for structural members according to this invention, it is possible not only to detect minute flaws on the surface of the balls and in the vicinity of the surface but also to achieve speedy, accurate and precise detection of minute flaws in the inside of the balls, which is necessary for quality control of the balls, thereby obtaining highly reliable balls for structural members.

EXAMPLES

Some embodiments of this invention will now be explained in detail below while referring to the drawings; it is to be understood, however, that the invention is not limited to the following embodiments.

EXAMPLE 1

FIG. 1 is a sectional view illustrating one embodiment of an ultrasonic testing apparatus for detecting flaws according to this invention, and FIG. 2 is a sectional view illustrating the positional relationship between two probes according to one embodiment of this invention.

Referring to FIG. 1, a ball mount portion having a recessed shape was formed by two pairs of rollers 11 supported by shafts 12, each of the rollers having a spherical surface portion with a diameter of 10 mm, parts cut away, and each pair of rollers being joined at the cut sections. The shafts 12, rollers 11 and bearings 13 for supporting the shafts 12 were all formed from zirconia.

The zirconia used for forming the shafts and the like had a Knoop hardness of 1200 kg/mm$^2$. The tips of the shafts and the bearings were finished to have a surface roughness $R_{max}$ of not more than 2 $\mu$m.

An ultrasonic testing apparatus for detecting flaws of balls for structural members comprising a ball driving motor 16 for rotating the ball driving rollers 11 through a bevel gearing 14 and a driving belt 15, probe mount arms 18-1 and 18-2 for fixing probes 17-1 and 17-2, respectively, and a probe driving motor 19 for swiveling the probes 17-1 and 17-2 around a ceramic ball 10 through the probe mount arms 18-1 and 18-2 was disposed in a water tank 20, which was filled with an appropriate quantity of water.

In FIG. 1, there are also shown a frame 24 for supporting the ball driving motor 16 and the probe driving motor 19, a frame 25 for supporting the ball driving rollers 11, and a structural member 26.

The two probes 17-1 and 17-2, as shown in FIG. 2(a), are both set with an eccentricity X upward from the center of the ball 10, and the foci of the probes are located at points a on the surface of the ball. While the ceramic ball 10 is rotated, the probes 17-1 and 17-2 are each swiveled along a line A on the peripheral surface of the ball 10 through respective flaw detecting ranges of 90°, thereby performing flaw detection over the entire surface of the ball 10. In this case, the probes 17-1 and 17-2 may both be set with an eccentricity downward from the center of the ball 10, to produce the same effect as above. Further, the probe 17-1 may be set with an eccentricity upward, and the probe 17-2 downward, from the center of the ball 10.

Figure 2B:
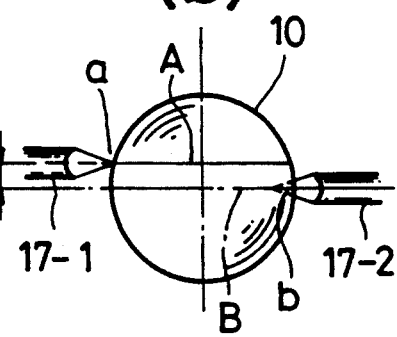

Moreover, in FIG. 2(b), the probe 17-1 is disposed with an upward eccentricity X, and the focus thereof is positioned at a point a on the surface of the ball 10, whereas the probe 17-2 is so placed that the center axis thereof conforms with the center of the ball 10 and the focus thereof is positioned at a point b inside the ball 10. In this case, while the ceramic ball 10 is rotated, the probes 17-1 and 17-2 are swiveled through 180° respectively along lines A and B on the peripheral surface of the ball 10, thereby performing flaw detection over the entire surface of the ball 10.

The direction of eccentricity of the probes is not limited to the above-mentioned directions, and may lie in any direction with respect to the surface of the ball.

In the ultrasonic testing apparatus for detecting flaws set as above, a silicon nitride ball 10 with 10 mm diameter was placed on the recessed form portion formed by the rollers 11. The probe 17-1 for ultrasonic flaw detection with a test frequency of 50 MHz, an oscillator diameter of 5 mm and a focal length of 10 mm was attached to the probe mount arm 18-1 at an arbitrary position, and the probe 17-2 for ultrasonic flaw detection with a test frequency of 50 MHz, an oscillator diameter of 5 mm and a focal length of 20 mm was attached to the probe mount arm 18-2 at an arbitrary position. Further, the probes 17-1 and 17-2 were connected to an ultrasonic flaw detector 21 by a cable 22.

Next, the ultrasonic flaw detector 21 was switched ON, and with observing a CRT 23, the probes 17-1 and 17-2 were moved horizontally, vertically, and back and forth in an adjusting manner so as to find positions at which the reflected waves (S waves) from the ball surface reach their maximum values, and the probes were again fixed in those positions. Further, the probe 17-1 was adjusted to an upward eccentricity of 1.3 mm, which was calculated according to the above-mentioned formula (1), with the velocity of ultrasonic longitudinal waves in water being 1500 m/sec and the velocity of ultrasonic transverse waves in the ball being 5800 m/sec. In addition, the probe 17-2 was moved by 6 mm toward the ball so as to locate the focus at a depth of 2 mm from the surface of the ball 10.

Subsequently, the ball driving motor 16 was operated to rotate the ball 10 at a rate of 300 rpm, and the probes 17-1 and 17-2 were swiveled at a rate of 5 rpm.

In the manner mentioned above, ten silicon nitride balls, Nos. 1 to 10, were tested to detect flaws. As a result, flaw echoes were observed for three of the balls, i.e., ball Nos. 3, 6 and 7. The detection waveforms in which the flaw echo was observed are shown in FIGS. 3, 4 and 5, respectively.

Figure 3A:
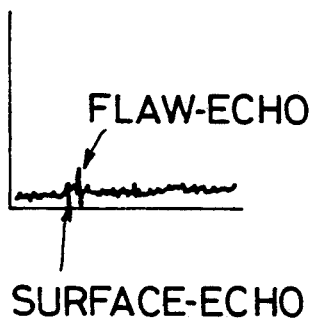
FIGS. 3(a), 3(b), 4(a), 4(b), 5(a) and 5(b) are each waveform charts obtained during testing, in the method for detecting flaws of balls according to one embodiment of this invention.
Figure 3B:
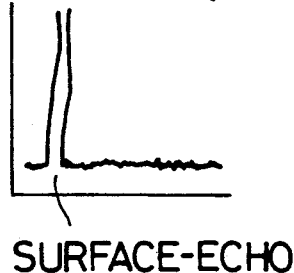

FIGS. 3(a) and 3(b) show flaw detection test waveform charts for ball No. 3, in which FIG. 3(a) is a test waveform chart obtained through the probe 17-1, and FIG. 3(b) through the probe 17-2. For the ball No. 3, the flaw echo was detected only through the probe 17-1, indicating that the flaw was present only on the ball surface. Upon microscopic observation, a pore flaw 45 μm in size was recognized on the surface of the ball.

Figure 4A:
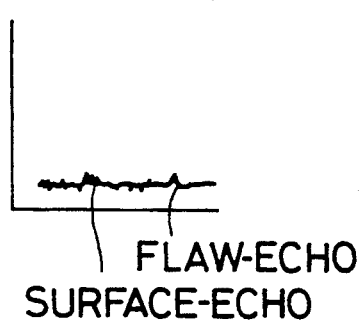
Figure 4B:
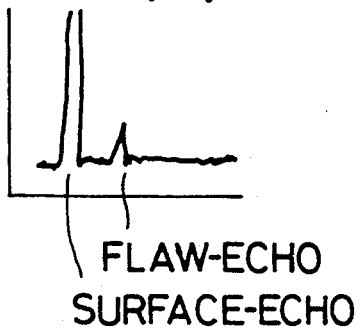

FIGS. 4(a) and 4(b) show flaw detection test waveform charts for ball No. 6, in which FIG. 4(a) is a test waveform chart obtained through the probe 17-1, and FIG. 4(b) through the probe 17-2. For the ball No. 6, the flaw echo was detected by both the probes 17-1 and 17-2. The waveform chart in FIG. 4(b) obtained through the probe 17-2 indicates the presence of a flaw at a depth of 2 mm from the surface of the ball. On the other hand, the waveform chart in FIG. 4(a) obtained through the probe 17-1 shows an echo, considered to be coming from the same flaw as above, at a distance of 2.5 mm from the ball surface and with an echo height of ⅓ times that in FIG. 4(b).

Figure 5A:
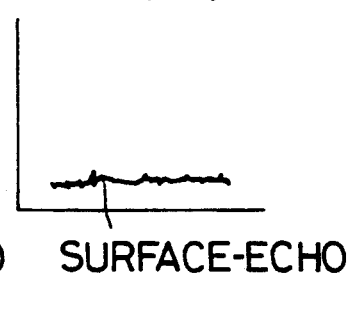
Figure 5B:
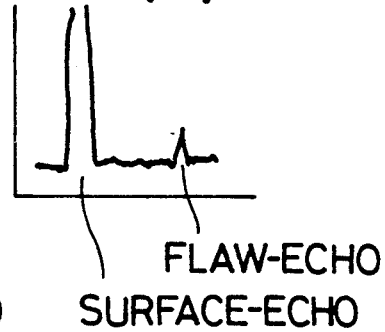

FIGS. 5(a)/show flaw detection test waveform charts for ball No. 7, in which FIG. 5(a) is a test waveform obtained through the probe 17-1, and FIG. 5(b) through the probe 17-2. For the ball No. 7, the flaw echo was detected only through the probe 17-2, indicating the presence of a flaw at a depth of 2.8 mm from the ball surface.

The portions for which the flaw echo was recognized in ball Nos. 6 and 7 were ground and observed, to confirm the presence of pore flaws 65 and 60 μm in size, respectively.

As seen clearly from the above results, the flaw echo from the flaw at a depth of 2 mm, as in the case of ball No. 6, appears greater in height on the waveform obtained by perpendicular beam testing through the probe 17-2 than on the waveform obtained by angle beam testing through the probe 17-1, In addition, the perpendicular beam testing gives a higher detection sensitivity, and makes it possible to specify the depth at which the flaw is present. Also, as seen from the detection results for ball No. 7, a flaw at a depth of more than 2 mm, even if as large as 100 μm or more in size, cannot be detected by the angle beam testing; however, such a flaw can be detected easily by the perpendicular beam testing. Thus, the ultrasonic testing method and apparatus for detecting flaws of balls according to this invention ensures a high degree of quality of the balls tested.

EXAMPLE 2

Probes 17-1 and 17-2 for ultrasonic flaw detection with a test frequency of 50 MHz, an oscillator diameter of 5 mm and a focal length of 10 mm were attached respectively to probe mount arms 18-1 and 18-2. Similarly to the manner in Example 1, the probes 17-1 and 17-2 were both disposed to have theirs respective foci positioned on the surface of the ball, with an eccentricity of 1.3 mm from the center of rotation of the ball, as shown in FIG. 2(a).

The ball No. 3 for which the flaw was detected in Example 1 was placed on a recessed portion formed by the rollers, and the test for flaw detection was carried out in the same manner as in Example 1 except that the swiveling angle of the probes was 95° and the swiveling rate was 2 rpm. As a result, flaws were detected at two locations. Observation under a microscope (×50) revealed the presence of pore flaws respectively of 45 and 35 μm in size.

What is claimed is:

1. An ultrasonic testing method for detecting flaws of balls for structural members, comprising the steps of:
   rotating a ball to be tested in a medium for transmitting ultrasonic waves;
   providing at least two focus-type ultrasonic probes each having a center axis set parallel to a rotational axis of said ball, wherein said probes are disposed in opposite directions to swivel along a periphery of said ball through a predetermined angle with respect to said rotational axis of said ball, wherein said probes are further disposed so as to detect respective non-overlapping flaw detecting regions on and/or in the ball, wherein one of said ultrasonic probes is disposed eccentrically with respect to said ball such that an angle of incidence of ultrasonic waves therefrom is a critical angle of the ultrasonic waves and the focus of the ultrasonic waves is on the surfae of said ball, and wherein another of said probes is disposed such that ultrasonic waves emitted therefrom are perpendicularly incident on the surface of said ball and the focus of the ultrasonic waves is located inside of said ball; and
   detecting flaws of the ball by sending ultrasonic waves from the probes toward the ball.

2. A method according to claim 1, wherein the ball is made of ceramic.

3. A method according to claim 1, wherein each said probe swivels about a swivelling axis perpendicular to said rotational axis of said ball, wherein said swivelling axis intersects said ball.

4. A method according to claim 3, wherein said swivelling axis intersects the center of said ball.

5. An ultrasonic testing apparatus for detecting flaws of balls for structural members, comprising:
   a ball holding means for rotatably holding a ball to be tested;
   at least two focus-type probes for detection of flaws on or in said ball;
   at least two probe mounting means for mounting the probes thereon so that respective axes of each of the probes can be set eccentrically relative to the center of the ball and wherein the focal position of each of the probes is variable, wherein one of said ultrasonic probes is disposed eccentrically with respect to said ball such that an angle of incidence of ultrasonic waves therefrom is a critical angle of the ultrasonic waves and the focus of the ultrasonic waves is on the surface of said ball, and wherein another of said probes is disposed such that ultrasonic waves ball, wherein one of said ultrasonic probes is disposed eccentrically with respect to said ball such that an angle of incidence of ultrasonic waves therefrom is a critical angle of the ultrasonic waves and the focus of the ultrasonic waves is on the surface of said ball, and wherein another of said probes is disposed such that ultrasonic waves emitted therefrom are perpendicularly incident on the surface of said ball and the focus of the ultrasonic waves is located inside of said ball; and detecting flaws of the ball by sending ultrasonic waves from the probes toward the ball.

6. An apparatus according to claim 5, wherein the probe mounting means are capable of being swiveled along a predetermined horizontal circumference of the peripheral surface of the ball held on the ball holding means.

7. An apparatus according to claim 5 or 6, wherein the ball holding portion comprises a plurality of rollers.

8. An apparatus according to claim 5 or 6, is disposed in a medium for transmitting ultrasonic waves.

9. An apparatus according to claim 5, wherein said swivelling axis of said probe driving means intersects through said ball.

10. An apparatus according to claim 9, wherein said swivelling axis intersects the center of said ball.

* * * * *